| United States Patent [19] | [11] Patent Number: 4,579,973 |
| Widmer et al. | [45] Date of Patent: Apr. 1, 1986 |

[54] PROCESS FOR THE MANUFACTURE OF CYCLOHEXENE DERIVATIVES

[75] Inventors: Erich Widmer, Münchenstein; Reinhard Zell, Rodersdorf, both of Switzerland

[73] Assignee: Hoffman-La Roche Inc., Nutley, N.J.

[21] Appl. No.: 699,874

[22] Filed: Feb. 8, 1985

Related U.S. Application Data

[63] Continuation of Ser. No. 434,193, Oct. 13, 1982, abandoned.

[30] Foreign Application Priority Data

Oct. 16, 1981 [CH] Switzerland ................. 6626/81

[51] Int. Cl.$^4$ .................. C07C 45/61; C07C 45/65
[52] U.S. Cl. ............................... 568/347; 568/338; 568/343; 568/376
[58] Field of Search ............... 568/347, 343, 338, 376, 568/823

[56] References Cited

U.S. PATENT DOCUMENTS

| 3,839,421 | 10/1974 | Schwieter et al. | 568/347 |
| 4,000,198 | 12/1976 | Rosenberger | 568/347 |
| 4,156,090 | 5/1979 | Kienzle | 560/61 |
| 4,193,850 | 3/1980 | Hengartner et al. | 204/79 |
| 4,323,711 | 4/1962 | Lukac et al. | 568/347 |
| 4,405,417 | 9/1983 | Grass et al. | 568/378 |

FOREIGN PATENT DOCUMENTS 0077439  4/1983  European Pat. Off. ............ 568/377

OTHER PUBLICATIONS

Surmatis et al., J. Org. Chem. 35, 1053 (1970).
Mayet et al., Helv. Chim. Acta., 50, 1606 (1967).
Surmatis et al., Helv. Chim. Acta., 53, 974 (1970).

*Primary Examiner*—Werren B. Lone
*Attorney, Agent, or Firm*—Jon S. Saxe; George M. Gould; William H. Epstein

[57] ABSTRACT

A novel process for the manufacture of cyclohexene derivatives which are suitable as intermediates for the manufacture of rhodoxanthin or zeaxanthin, as well as a process for the manufacture of rhodoxanthin or of zeaxanthin itself. The invention is also concerned with a novel starting material and novel intermediates in this process.

14 Claims, No Drawings

PROCESS FOR THE MANUFACTURE OF CYCLOHEXENE DERIVATIVES

This is a continuation of application Ser. No. 434,193, filed Oct. 13, 1982, now abandoned.

BACKGROUND OF THE INVENTION

The term zeaxanthin as used in this specification means (3RS,3'RS)-zeaxanthin.

Rhodoxanthin is a naturally occurring carotenoid which can be used, inter alia, as a foodstuff coloring substance. Zeaxanthin, the (3R,3'R) antipode of which occurs in nature, can also be used as a foodstuff coloring substance (e.g. for egg yolk pigmentation).

Hitherto known synthesis for the manufacture of these two carotenoids, i.e. rhodoxanthin and zeaxanthin, require about 10 to 18 steps. By means of the process provided by the present invention, these substances can now be manufactured in a substantially simpler manner.

SUMMARY OF THE INVENTION

The process provided by the present invention comprises converting a compound of the formula

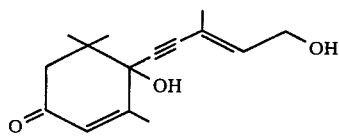

I in the presence of a strongly basic, homogeneous, aqueous-organic solvent mixture containing an effective amount of zinc into a compound of the formula

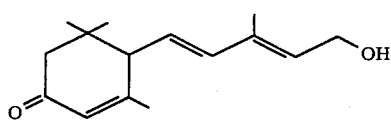

II if desired, reacting compounds of formula II, after conversion into a phosphonium salt of the formula

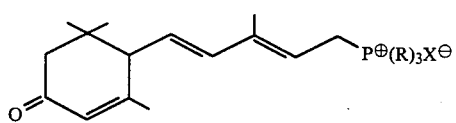

III wherein R represents phenyl and X represents chlorine, bromine or iodine,
with a dialdehyde of the formula

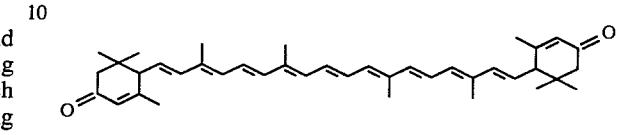

IV to provide a compound of the formula

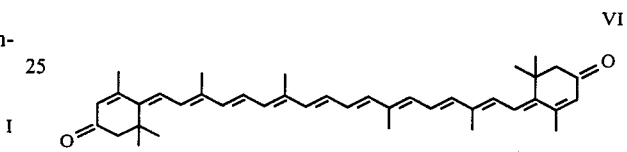

V

In providing the compound of formula V, the reaction is achieved by a reaction between at least two molecules of a compound of formula III and one molecule of a compound of formula IV.

If desired, the compound of formula V may be dehydrogenated to provide rhodoxanthin of the formula

VI and, if desired, this rhodoxanthin may be reduced to provide zeaxanthin of the formula

VII

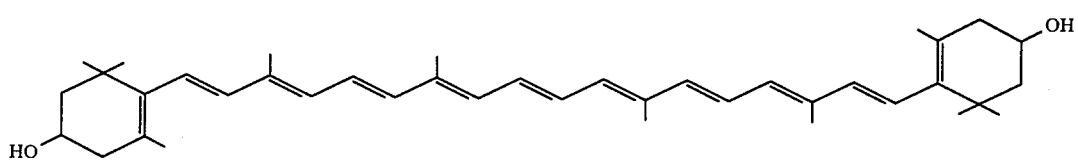

The compounds of formulae I, II and III are novel compounds of the present invention.

DETAILED DESCRIPTION OF THE INVENTION

The conversion of the compound of formula I into the compound of formula II involves a reductive elimination of the angular hydroxy group and simultaneous partial reduction of the triple bond.

This conversion is carried out in accordance with the invention in a reaction containing the compound of formula I and zinc in a strongly basic, homogeneous, aqueous-organic solvent mixture. This reaction can be carried out not only where said solvent mixture contains the compound of formula I and zinc alone, but also in one having the compound of formula I and zinc in the presence of a complex former. As complex formers there can be used especially alkali metal cyanides such as lithium sodium or potassium cyanide. Furthermore, ethylenediaminetetraacetic acid (EDTA), ethylenediamine, nitrilotriacetic acid, oxalic acid, o-phenanthroline and the like can be used as the complex former. Strongly complexing substances (i.e. those having pK values for the zinc complex in aqueous solution of greater than 9 are preferred.

As mentioned earlier, the reaction, i.e. the conversion of compound of formula I to a compound of formula II, may be carried out under basic conditions. It is preferred that the basic conditions be strongly basic conditions, especially at pH values of about 13 to 14, preferably at pH values of about 13.5–14 and particularly at pH 14. These pH values can be achieved in a manner known per se; for example, by adding an inorganic base such as, for example, sodium or potassium hydroxide and the like to aqueous-organic solvent mixture to provide a strongly basic, homogeneous aqueous-organic solvent mixture. When the reaction is carried out in the presence of a complex former, these conditions can be achieved under certain circumstances by the complex former.

Any effective amount of zinc may be used to carry out the conversion of a compound of formula I to a compound of formula II. The effective amount of zinc used in the process is conveniently from about 2 to about 10 mol, preferably from about 5 to about 8 mol, per mol of the compound of formula I. When a complex former is used, this is preferably added in an amount of about 0.1 to about 1 mol, especially about 0.5 to about 0.8 mol, per mol of the compound of formula I.

Any aqueous organic solvent capable of being strongly basic and homogeneous may be used. Among such aqueous-organic solvent-mixtures there can be used water-miscible inert organic solvents especially lower alcohols, i.e. alkanols containing 1-4 carbon atoms, namely methanol, ethanol, n-propanol, iso-propanol and n-butanol. Dioxan, tetrahydrofuran, acetone, dimethyl sulfoxide, dimethylformamide and the like can also be used. However, the lower alkanols, especially methanol, ethanol and n-propanol, are preferred. The ratio of solvent to water is defined by the solubility of the compound of formula I in the particular solvent-water mixture. However, the ratio conveniently lies between about 4:1 to 1:4 (v/v).

The reaction can be carried out in the presence or absence of a protective gas atmosphere. The reaction is preferably carried out under an inert gas atmosphere such as, for example, nitrogen, argon and the like. Furthermore, the reaction is conveniently carried out at a temperature of about 0° C. to about 50° C., preferably at about 15° C. to about 30° C. and especially at about room temperature.

In the conversion of the compound of formula II into a phosphonium salt of formula III, the allylic hydroxyl group in the compound of formula II is firstly replaced by halogen. In other words a compound of formula II is converted by a replacement reaction replacing the allylic hydroxyl of the compound of formula II with a halogen. This replacement may be achieved by reacting the compound of formula II with an effective amount of a halide suitable for such replacement reactions. In the replacement reaction the compound of formula II is converted to a halide of the formula:

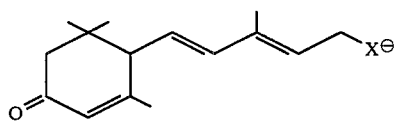

II' wherein X is a halogen selected from a group consisting of chlorine, bromine and iodine.

This replacement can be carried out for example in a manner known per se by means of a hydrogen halide (hydrogen chloride, hydrogen bromide or hydrogen iodide) in aqueous solution (e.g. 37%, 48% or 57%).

The replacement can be carried out at temperatures between about −20° C. and about +25° C., preferably at about 0° C. As the solvent for this reaction there can be used a solvent which is suitable for such replacement reactions, for example a chlorinated hydrocarbons such as methylene chloride, chloroform and the like.

The conversion of a thus-obtained halide into a phosphonium salt of formula III can be carried out in a manner known per se. The reaction is conveniently carried out using a triarylphosphine, especially triphenyl-phosphine, in a suitable inert organic solvent such as, for example, a chlorinated hydrocarbon (e.g. methylene chloride or chloroform) or an ester of a lower carboxylic acid containing 1 to 4 carbon atoms (e.g. ethyl formate, ethyl acetate etc). Furthermore, the reaction is preferably carried out under an inert atmosphere and at about room temperature or at an elevated temperature. The temperature is, however, of no critical significance in this reaction.

The reaction of a phosphonium salt of formula III with the dialdehyde of formula IV to give the compound of formula V can be carried out in a manner known per se; that is to say, under the conditions which are usual in the case of Wittig reactions. The reaction is conveniently carried out in a chlorinated hydrocarbon such as, for example, methylene chloride or chloroform and in the presence of a base such as, for example, sodium methylate. In this case it is advantageous to add the base to the reaction mixture not all at once, but slowly and continuously.

The dehydrogenation of the compound of formula V to give rhodoxanthin of formula VI can be carried out in a manner known per se; for example, in accordance with the oxidation of dihydrorhodoxanthin to rhodoxanthin which is described by Kuhn and Brockmann in Ber. 66, 1319 (1933).

The reduction of rhodoxanthin of formula VI to give zeaxanthin of formula VII can also be carried out in a manner known per se; for example, in accordance with Karrer and Solmssen, Helv. Chim. Acta 18, 477 (1935).

The compound of formula I which is used as the starting material in the process provided by the present invention is novel and is also an object of the present invention. It can be prepared starting from ketoisophorone of the formula

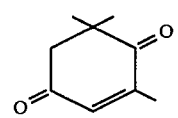

VIII by reaction with the compound of the formula

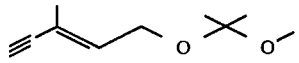

IX

This reaction is conveniently carried out via the lithium or magnesium salt of the compound of formula IX in an inert organic solvent for organometal compounds such as, for example, open or cyclic ethers (e.g. diethyl ether, dioxan and tetrahydrofuran) or aromatic hydrocarbons (e.g. benzene, toluene and the like) or also in liquid ammonia. The reaction is preferably carried out at a temperature of about −50° C. to about room temperature. The ketoisophorone used in the reaction must be protected in the 3-position (e.g. in the form the lithium enolate or as a monoketal and the like).

The following Examples are meant to further illustrate the present invention but are not meant to restrict the invention in scope or spirit:

EXAMPLE 1

44.3 g (0.178 mol) of 4-hydroxy-4-(5-hydroxy-3-methyl-3-penten-1-ynyl)-3,5,5-trimethyl-2-cyclohexen-1-one were dissolved in 800 ml of n-propanol/water (1:1, v/v) in a 1.5 liter sulphonation flask provided with stirrer, thermometer and gasification headpiece, treated with 5.88 g of sodium cyanide (0.12 mol) and 77.4 g of zinc powder (1.18 g-atoms) and stirred vigorously at room temperature with occasional slight cooling until the reaction was complete (about 5 hours). The resulting suspension was then suction filtered under argon and the resulting residue was washed three times with 100 ml of methylene chloride each time and twice with 100 ml of deionized water each time. The resulting filtrate was added to a 1-liter separating funnel $S_1$ with the aid of 50 ml of methylene chloride. Two further 1 liter separating funnels ($S_2$ and $S_3$) were each charged with 100 ml of saturated sodium chloride solution. Thereupon, the organic phase from $S_1$ as well as two 100 ml portions of methylene chloride were passed in succession with good intermixing through the three separating funnels $S_1$ to $S_3$. The organic phases were combined and dried over 50 g of sodium sulphate. Thereupon, the mixture was suction filtered, the residue was washed twice with 50 ml of methylene chloride each time and the filtrates were dried to constant weight in a rotary evaporator under a water-jet vacuum at a bath temperature of 40° C. There were obtained 47.9 g of crude product which, for purification, was adsorbed on silica gel and chromatographed with hexane/ether. There were thus obtained 33.9 g (81.3%) of 4-(5-hydroxy-3-methyl-1,3-pentadienyl)-3,5,5-trimethyl-2-cyclohexen-1-one in the form of an oil. The structure of this compound was characterized unequivocally by microanalysis, NMR, IR and MS spectra.

The 4-hydroxy-4-(5-hydroxy-3-methyl-3-penten-1-ynyl)-3,5,5-trimethyl-2-cyclohexen-1-one used as the starting material in the above process can be prepared as follows:

250 ml of ammonia were condensed in a 750 ml sulfphonation flask provided with stirrer, thermometer, ammonia condenser and a 100 ml dropping funnel with pressure balance and gasification headpiece and then treated with 0.1 g of iron (III) nitrate. A total of 3.2 g of lithium wire (0.46 g-atoms) were thereupon added in portions in about 15 minutes. The resulting mixture was further stirred at −40° C. until the reaction to lithium amide was complete (about 20 minutes). Subsequently, there was added dropwise in about 20 minutes while cooling with an acetone/dry-ice bath at −40° C. a solution of 77.4 g of acetone methyl 3-methyl-2-penten-4-ynyl acetal in 20 ml of absolute ether, followed by 30.4 g of 2,6,6-trimethyl-2-cyclohexen-1,4-dione in 20 ml of absolute ether. The mixture was stirred at −40° C. until the reaction was complete (about 2.5 hours). 200 ml of absolute ether were now added to the mixture and subsequently ammonia was driven off with the aid of a warm water bath. As soon as the mixture had reached room temperature, it was cooled further to 0° C. with an ice bath and hydrolyzed by the dropwise addition of 100 ml of deionized water. For the further working-up, the mixture was rinsed into a 1 liter separating funnel $S_1$ with the aid of 100 ml of ether. Two further 500 ml separating funnels ($S_2$ and $S_3$) were each charged with 200 ml of ether. Thereupon, firstly the aqueous phase from $S_1$ as well as three 100 ml portions of semi-saturated sodium chloride solution were passed in succession and with good intermixing through the three separating funnels $S_1$ to $S_3$. The resulting organic extracts were combined and dried over 50 g of sodium sulphate. Thereupon, the mixture was suction filtered, the drying agent was rinsed on the suction filter with 50 ml of ether and the filtrates were concentrated in a rotary evaporator at the water-jet vacuum at 30° C. The residue was subsequently concentrated up to constant weight in a rotary evaporator with dry-ice condenser under a fine vacuum (about 0.1 mbar) at 65° C. There were thus obtained 62 g (96.8%) of a reaction product in the form of a dark oil.

For the hydrolysis, these 62 g of reaction product were taken up in 100 ml of acetone and treated dropwise with 50 ml of 3N sulphuric acid in 15 minutes at 0° C. while stirring and gassing with argon. The black mixture was washed into a 500 ml separating funnel $S_1$ with the aid of 100 ml of ether and then treated with 200 ml of semi-saturated sodium chloride solution and shaken well. Two further 500 ml separating funnels ($S_2$ and $S_3$) were each charged with 200 ml of ether. Thereupon, the resulting aqueous phase from $S_1$ as well as two 100 ml portions of semi-saturated sodium chloride solution were passed in succession with good intermixing through the three separating funnels $S_1$ to $S_3$. The organic phases were combined and dried over 50 g of sodium sulphate. Thereupon, the mixture was suction filtered, the drying agent was rinsed on the suction filter with 50 ml of ether and the filtrates were concentrated to constant weight in a rotary evaporator under a water-jet vacuum at 30° C. There were thus obtained 49.1 g (99.0%) of 4-hydroxy-4-(5-hydroxy-3-methyl-3-penten-1-ynyl)-3,5,5-trimethyl-2-cyclohexen-1-one in the form of a light brownish oil.

EXAMPLE 2

A solution of 24.8 g (94.6 mmol) of 4-hydroxy-4-(5-hydroxy-3-methyl-3-penten-1-ynyl)-3,5,5-trimethyl-2-cyclohexen-1-one (prepared in accordance with Example 1) in 450 ml of n-propanol/water (1:1, v/v) was placed in a 1 liter four-necked flask provided with stirrer, thermometer, 250 ml dropping funnel with pressure balance and gasification headpiece. With stirring and argon gasification there were added firstly 13 g (47.2 mmol) of nitrileotriacetic acid trisodium salt and then 33 g (0.50 g-atoms) of zinc powder. 300 ml (0.3 mol) of 1N sodium hydroxide were then added dropwise at room temperature in about 20 minutes and the mixture was subsequently stirred for a further 4 hours. Thereafter, the resulting suspension was suction filtered under argon and the residue was washed three times with 100 ml of methylene chloride each time and twice with 100 ml of deionized water each time. The resulting filtrate was added to a 2 liter separating funnel $S_1$ with the aid of 100 ml of methylene chloride. Two further 1 liter separating funnels ($S_2$ and $S_3$) were each charged with 200 ml of saturated sodium chloride solution. Thereupon, firstly the organic phase from $S_1$ as well as two 200 ml portions of methylene chloride were passed in succession and in each case with good intermixing through the three separating funnels $S_1$–$S_3$. The organic phases were combined and dried over 100 g of sodium sulfate. Thereupon, the resulting mixture was suction filtered, the residue therefrom was washed twice with 100 ml of methylene chloride each time and the filtrates were dried to constant weight in a rotary evaporator under a water-jet vacuum at a bath temperature of 40° C. There were obtained 21.1 g of crude product which is identical with the product manufactured in accordance with Example 1.

EXAMPLE 3

10 g (40 mmol) of 4-hydroxy-4-(5-hydroxy-3-methyl-3-penten-1-ynyl)-3,5,5-trimethyl-2-cyclohexen-1-one (prepared in accordance with Example 1) were dissolved in 200 ml of n-propanol/water (1:1, v/v) under argon in a 500 ml multi-necked flask provided with stirrer, thermometer, dropping funnel and gasification headpiece and treated with 20.9 g (0.32 g-atoms) of zinc powder. Thereupon, 120 ml (0.12 mol) of 1N sodium hydroxide solution were added dropwise thereto in 5 minutes at room temperature while stirring and the mixture was stirred for a further 1 hour. The resulting mixture was then worked-up in a manner analogous to that described in Example 1 and there were obtained 9.2 g of crude product. The purification on silica gel in a manner analogous to that described in Example 1 gave 6.9 g (74.3%) of 4-(5-hydroxy-3-methyl-1,2-pentadienyl)-3,5,5-trimethyl-2-cyclohexen-1-one in the form of an oil. The structure of this compound was characterized unequivocally by microanalysis, NMR, IR and MS spectra.

EXAMPLE 4

(A) 46.6 g (0.2 mol) of 4-(5-hydroxy-3-methyl-1,3-pentadienyl)-3,5,5-trimethyl-2-cyclohexen-1-one (prepared in accordance with Example 1 or 2), dissolved in 200 ml of methylene chloride, were placed in a 1.5 liter sulphonation flask provided with stirrer, thermometer, 500 ml dropping funnel with pressure balance and an apparatus for inert gasification and treated dropwise with a total of 124 ml of 37% hydrochloric acid at $-5°$ C. to 0° C. in about 20 minutes while stirring well and gassing with argon. Thereupon, the the resulting mixture was stirred for a further 15 minutes at 0° C. until the reaction was complete. Subsequently, the resulting dark mixture was transferred into a 1 liter separating funnel $S_1$ with the aid of 200 ml of methylene chloride. Two further 1 liter separating funnels ($S_2$ and $S_3$) were each charged with 250 ml of saturated sodium bicarbonate solution. Thereupon, the lower organic phase from $S_1$, as well as two 250 ml portions of methylene chloride were passed with good intermixing through the three separating funnels $S_1$ to $S_3$. The organic phases were thereupon combined, dried over 50 g of sodium sulphate, suction filtered and the drying agent was rinsed on the suction filter with 50 ml of methylene chloride. The filtrate was then concentrated to a volume of about 100 ml in a rotary evaporator under a water-jet vacuum at 30° C. (bath temperature).

(B) A solution of 52.4 g (0.2 mol) of triphenylphosphine in 100 ml of methylene chloride was placed in a 2.5 liter sulphonation flask provided with stirrer, thermometer, 250 ml dropping funnel with pressure balance and an apparatus for inert gasification. With stirring and inert gasification there was then added dropwise within about 10 minutes the methylene chloride solution obtained in accordance with paragraph (A). The resulting dark solution was subsequently stirred at room temperature for a further 21 hours and then concentrated to a volume of about 200 ml in a rotary evaporator under a water-jet vacuum at 30° C. (bath temperature). Subsequently, to this concentrated solution a total of 850 ml of ethyl acetate were added dropwise in about 30 minutes at room temperature with stirring and argon gasification, crystallization soon beginning. The resulting suspension was then stirred at room temperature for 24 hours and in ice for 2 hours, suction filtered, the product on the suction filter was washed thoroughly with two 100 ml portions of ethyl acetate and then dried to constant weight in a drying oven under a water-jet vacuum at 40° C. The resulting crystals were subsequently recrystallized from methylene chloride/ethyl acetate and there were obtained 63.3 g (61.7%) of [3-methyl-5-(2,6,6-trimethyl-4-oxo-2-cyclohexen-1-yl)-2,4-pentadienyl]triphenylphosphonium chloride of melting point 164°–166° C.

EXAMPLE 5

(A) 2.08 g (8.9 mmol) of 4-(5-hydroxy-3-methyl-1,3-pentadienyl)-3,5,5-trimethyl-2-cyclohexen-1-one, dissolved in 10 ml of methylene chloride, were placed in a 50 ml multi-necked round flask provided with stirrer, thermometer, 10 ml dropping funnel with pressure balance and an apparatus for inert gasification and treated dropwise at $-15°$ C. during 10 minutes with a total of 4.8 ml of 63% hydrobromic acid. Thereafter, the resulting mixture was stirred at $-15°$ C. for about a further 30 minutes. Subsequently, the resulting dark mixture was transferred into a 50 ml separating funnel $S_1$ with the aid of 25 ml of methylene chloride. Two further 50 ml separating funnels ($S_2$ and $S_3$) were each charged with 25 ml of saturated sodium bicarbonate solution. Now, the lower organic phase from $S_1$ as well as two 25 ml portions of methylene chloride were passed with good intermixing through the three separating funnels $S_1$ to $S_3$. The organic phases were combined, dried over 25 g of sodium sulphate, then suction filtered, the drying agent was rinsed on the suction filter with 25 ml of methylene chloride and the filtrate was concentrated to a volume of about 10 ml in a rotary evaporator under a water-jet vacuum at 30° C. (bath temperature).

(B) 2.89 g (11 mmol) of triphenylphosphine in 10 ml of methylene chloride were placed in a 50 ml round flask provided with stirrer, thermometer, 10 ml dropping funnel with pressure balance and an apparatus for inert gasification. With stirring and gassing with argon there was then added dropwise in about 10 minutes the methylene chloride solution obtained in accordance with paragraph (A). The resulting dark solution was subsequently stirred at room temperature for about 2 hours and then concentrated to a volume of about 20 ml in a rotary evaporator under a water-jet vacuum at 30° C. (bath temperature). Subsequently, to the concentrated solution a total of 100 ml of ethyl acetate were added dropwise in about 1 hour at room temperature with stirring and argon gasification. Thereupon, the resulting suspension was seeded, stirred at room temperature for 24 hours and in ice for 2 hours and then suction filtered. The resulting suspension was seeded, stirred at room washed thoroughly with two 25 ml portions of ethyl acetate and then dried to constant weight in a drying oven under a water-jet vacuum at 40° C. There were obtained 4.2 g (84.3%) of [3-methyl-5-(2,6,6-trimethyl-4-oxo-2-cyclohexen-1-yl)-2,4-pentadienyl]triphenylphosphonium bromide of melting point 168°–170° C.

EXAMPLE 6

(A) 103 g (0.20 mol) of [3-methyl-5-(2,6,6-trimethyl-4-oxo-2-cyclohexen-1-yl)-2,4-pentadienyl]triphenylphosphonium chloride and 13.1 g (79.8 mmol) of 2,7-dimethyl-octatriene-(2,4,6-dial-(1,8), dissolved in 800 ml of methylene chloride, were placed in a 1.5 liter sulphonation flask provided with stirrer, thermometer, 50 ml dropping funnel with pressure balance and an apparatus for inert gasification. While stirring, gassing with argon and cooling at −20° C. there were now added dropwise in the course of 2 hours a total of 46 ml of 10% sodium methylate solution. The resulting mixture was subsequently stirred at 0° C. for a further 2 hours. The reaction of the mixture was quenched by adding 12 ml of glacial acetic acid. Three 2-liter separating funnels $S_1$ to $S_3$ were each charged with 500 ml of saturated sodium chloride solution. Then, firstly the reaction solution and the two 500 ml portions of methylene chloride were passed with vigorous intermixing through the three separating funnels $S_1$ to $S_3$. The organic extracts were combined, dried over 100 g of sodium sulphate, suction filtered and the drying agent was rinsed twice on the suction filter with 200 ml of methylene chloride.

(B) The filtrate obtained in accordance with paragraph (A) was placed in a 1.5 liter sulphonation flask provided with stirrer, thermometer, 250 ml dropping funnel with pressure balance and apparatus for inert gasification as well as a distillation headpiece. While stirring and heating (120° C.) and under argon, the solution was concentrated at normal pressure to a volume of about 500 ml. Then, with continuous distillation at a constant volume of about 500 ml there were added dropwise about 1.8 l of methanol until the boiling point of 63° C. had been reached. A product crystallized out during this procedure. The distillation headpiece was subsequently replaced by a reflux condenser and the suspension was stirred at reflux for 3 days. The resulting mixture was then cooled to −20° C. and suction filtered. The crystals were washed thoroughly on the suction filter with three 100 ml portions of methanol (at −20° C.) with argon gasification, sucked dry and dried to constant weight in a drying oven under a water-jet vacuum at 30° C. There were obtained 32 g (71%) of 1,18-bis(4-oxo-2,6,6-trimethyl-2-cyclohexen-1-yl)-3,7,12,16-tetramethyl-1,3,5,7,9,11,13,15,17-octadecanonaene of melting point 185°–187° C.

In a manner analogous to the foregoing, this compound can also be prepared starting from [3-methyl-5-(2,6,6-trimethyl-4-oxo-2-cyclohexen-1-yl)-2,4-pentadienyl]triphenylphosphonium bromide.

EXAMPLE 7

(A) 11.3 g (20 mmol) of 1,18-bis(4-oxo-2,6,6-trimethyl-2-cyclohexen-1-yl)-3,7,12,16-tetramethyl-1,3,5,7,9,11,13,15,17-octadecanonaene were dissolved in 200 ml of pyridine at 70° C. under argon in a 500 ml multi-necked flask provided with a magnetic stirrer, 50 ml dropping funnel and thermometer, cooled to room temperature, stirred at 0° C. with access of air for 20 minutes and then treated dropwise during 10 minutes with 50 ml of a 1N ethanolic potassium hydroxide solution. The resulting mixture was then stirred for a further 30 minutes in ice and for 1.5 hours at room temperature with free access of air. The resulting solution was then transferred into a 1 liter separating funnel $S_1$ with the aid of 200 ml of methylene chloride which contained 400 ml of a 5% sodium chloride solution. Two further 1 liter separating funnels ($S_2$ and $S_3$) were each charged with 500 ml of 3N hydrochloric acid. Now, the lower organic phase from $S_1$ as well as three 200 ml portions of 200 ml of methylene chloride were passed with good intermixing through the three separating funnels ($S_1$ to $S_3$). The organic extracts were washed with 400 ml of deionized water and 400 ml of 2% sodium bicarbonate solution, dried over 100 ml of sodium sulphate and suction filtered. The drying agent was rinsed on the suction filter with two 200 ml portions of methylene chloride and the filtrate was concentrated to a volume of about 100 ml in a rotary evaporator under a water-jet vacuum at 30° C. to provide a methylene chloride solution.

(B) The methylene chloride solution (100 ml) obtained in accordance with paragraph (A) was placed in a 350 ml sulphonation flask provided with stirrer, thermometer, 100 ml dropping funnel with pressure balance and apparatus for inert gasification as well as a distillation headpiece. With stirring and distillation, the resulting mixture was concentrated at normal pressure to a residual volume of about 100 ml. While maintaining this volume, deionized water was subsequently added dropwise until the boiling point had reached 93° C. (bath temperature=130° C.). The resulting sticky mass was then stirred at reflux for 48 hours, cooled to room temperature and then dissolved with the aid of about 200 ml of methylene chloride. After separating the resulting phases in a 500 ml separating funnel, the organic phase was dried over 25 g of sodium sulfate (drying agent) and suction filtered. The drying agent was rinsed on the suction filter with two 100 ml portions of methylene chloride and the filtrate was concentrated to a volume of about 50 ml in a rotary evaporator under a water-jet vacuum at 300° C. This resulting solution was treated with 150 ml of ethyl acetate, whereupon the resulting mixture was concentrated to a volume of about 50 ml in a rotary evaporator under a water-jet vacuum at 40° C. (bath temperature). In so doing, product began to crystallize out. The suspension was subsequently stirred at 0° C. for a further 2 hours and then suction filtered. The crystals on the suction filter were washed thoroughly with two 50 ml portions of ethyl acetate and then dried to constant weight in a drying oven under a water-jet vacuum at 30° C. There were obtained 6.3 g (56%) of rhodoxanthin of melting point 208°–210° C.

We claim:

1. A process for producing a cyclohexene derivative of the formula:

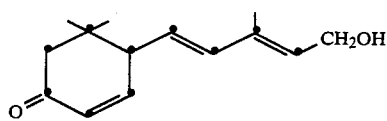

II comprising reducing a compound of the formula:

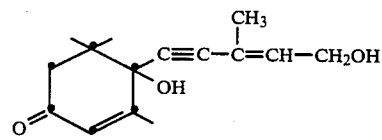

I by means of a reducing agent which is zinc to form said compound of formula II, said reduction being carried out in a strongly basic homogeneous organic solvent medium at a pH of from 13 to 14.

2. A process according to claim 1, wherein the reaction is carried out at pH 14.

3. A process according to claim 1, wherein the organic solvent in the water-organic solvent mixture is selected from a group consisting of a lower alcohol containing 1 to 4 carbon atoms, dioxan, tetrahydrofuran, acetone, dimethyl sulfoxide and dimethylformamide.

4. A process according to claim 3, wherein the solvent is a lower alcohol containing 1 to 4 carbon atoms.

5. A process according to claim 4, wherein the lower alcohol is selected from the group consisting of methanol, ethanol and n-propanol.

6. A process according to claim 1 wherein the conversion of the compound of formula I into the compound of formula II is carried out in the presence of a complex former.

7. A process according to claim 6, wherein the complex former is selected from the group consisting of an alkali metal cyanide, ethylenediaminetetraacetic acid, ethylenediamine, nitrilotriacetic acid and p-phenanthroline.

8. A process according to claim 7, wherein the alkali metal cyanide is sodium cyanide or potassium cyanide.

9. A process according to claim 1, wherein the solvent in the aqueous-organic solvent mixture is selected from a group consisting of a lower alcohol containing 1 to 4 carbon atoms, dioxan, tetrahydrofuran, acetone, dimethyl sulfoxide and dimethylformamide.

10. A process according to claim 9, wherein the solvent is a lower alcohol containing 1 to 4 carbon atoms.

11. A process according to claim 1, wherein the conversion of the compound of formula I into the compound of formula II is carried out in the presence of a complex former.

12. A process according to claim 11, wherein the complex former is selected from the group consisting of an alkali metal cyanide, ethylenediaminetetraacetic acid, ethylenediamine, nitrilotriacetic acid and p-phenanthroline.

13. A process according to claim 12, wherein the alkali metal cyanide is sodium cyanide or potassium cyanide.

14. The process of claim 1 wherein the organic solvent medium contains a mixture of an organic solvent and water.

* * * * *